United States Patent
Duan et al.

(10) Patent No.: US 8,465,757 B2
(45) Date of Patent: Jun. 18, 2013

(54) NANOEMULSION OF RESVERATROL-PHOSPHOLIPID COMPLEX AND METHOD FOR PREPARING THE SAME AND APPLICATIONS THEREOF

(75) Inventors: Mingxing Duan, Beijing (CN); Huafeng Zhou, Changshu (CN); Zemin Yan, Changshu (CN)

(73) Assignees: Tsinghua University, Beijing (CN); Jiangsu Longliqi Bioscience Co. Ltd., Jiangsu (CN)

( * ) Notice: Subject to any disclaimer, the term of this patent is extended or adjusted under 35 U.S.C. 154(b) by 632 days.

(21) Appl. No.: 12/569,740

(22) Filed: Sep. 29, 2009

(65) Prior Publication Data

US 2010/0297199 A1    Nov. 25, 2010

(30) Foreign Application Priority Data

May 20, 2009 (CN) .......................... 2009 1 0084272

(51) Int. Cl.
*A61K 8/02* (2006.01)
(52) U.S. Cl.
USPC ........................................................ 424/401
(58) Field of Classification Search
None
See application file for complete search history.

(56) References Cited

U.S. PATENT DOCUMENTS

| 5,085,854 | A  | * | 2/1992 | Fukuda et al. | 424/63 |
| 5,716,637 | A  | * | 2/1998 | Anselem et al. | 424/450 |
| 2003/0078238 | A1 | * | 4/2003 | Yoo et al. | 514/100 |
| 2004/0116386 | A1 | * | 6/2004 | Pifferi et al. | 514/78 |
| 2011/0009496 | A1 | * | 1/2011 | Lunsmann et al. | 514/729 |

FOREIGN PATENT DOCUMENTS

CN    101095664 A    6/2006

* cited by examiner

*Primary Examiner* — Carlos Azpuru
*Assistant Examiner* — Casey Hagopian
(74) *Attorney, Agent, or Firm* — John B. Hardaway, III; Nexsen Pruet, LLC

(57) ABSTRACT

The present invention relates to a nanoemulsion of resveratrol-phospholipid complex, method for preparing the same and applications thereof. The nanoemulsion comprises: 1 part by weight of resveratrol, 2~30 parts by weight of phospholipid, and 30~490 parts by weight of an aqueous solution of polyol with the polyol concentration being 30~99 percent by weight. The method comprises the steps of: a resveratrol-phospholipid complex being prepared, then the complex being dispersed into the aqueous solution of polyol to form a dispersion, and a nanoemulsion with particle size less than 200 nm being formed by homogenization of the dispersion with a high pressure homogenizer or Microfluidizer homogenizer. The nanoemulsion is miscible with water at any ratio, has high stability and high bioavailability, and thus can be widely used for preparation of cosmetics, pharmaceuticals or healthcare products.

8 Claims, No Drawings

NANOEMULSION OF RESVERATROL-PHOSPHOLIPID COMPLEX AND METHOD FOR PREPARING THE SAME AND APPLICATIONS THEREOF

CROSS-REFERENCE TO RELATED APPLICATIONS

Applicants claim priority to the Chinese Application Number 200910084272.3 filed May 20, 2009.

FIELD OF THE INVENTION

The present invention relates to a biological nanoemulsion useful in the preparation for cosmetics, pharmaceuticals, or health products, more particularly to a nanoemulsion of resveratrol-phospholipid complex, and to a method for preparing the same and the applications thereof.

BACKGROUND OF THE INVENTION

Resveratrol is a non-flavonoid polyphenol having stilbene structure, and is an anti-toxin synthesized by plants under stress. Resveratrol is a natural anti-oxidant that can reduce blood viscosity, inhibit platelet coagulation and improve vasodilation to maintain blood flow; and it can prevent the occurrence and development of cancer, and is effective for the prevention and treatment of atherosclerosis, coronary heart disease, ischemic heart disease, and high blood cholesterol. In addition, resveratrol also has estrogen-like effects, thus can be used for the treatment of breast cancer. Recently, the resveratrol becomes widely useful in pharmaceutical and food industry, and has highly potential value in market. The bioavailability of resveratrol is low, due to its water-insoluble and lipid-insoluble property, which reduces its efficacy and limits its applications.

Phospholipid complex (Phytosome) is a more stable complex formed by a pharmaceutical with a phospholipid through charge transfer between the pharmaceutical and the phospholipid molecule. Phospholipid complex, as a new type pharmaceutical formulation, can significantly improve the lipid-solubility absorption, and bioavailability of the pharmaceutical, and reduce the side effects of the pharmaceutical. Although the phospholipid complex can improve the lipid-soluble index of pharmaceuticals, it is difficult to be dissolved in water, especially when the phospholipid complex is in a form of a formulation of high concentration.

U.S. Patent Application US2004116386A1 disclosed a resveratrol phospholipid complex and a preparation method thereof. Chinese Patent Application Publication No. CN101095664 also disclosed a resveratrol phospholipid complex, its preparation method and applications. According to the disclosure of either of the two patent publications, the resveratrol-phospholipid complex renders lipophilic property to the lipid-insoluble resveratrol, and thus can increase the lipid-soluble index of the resveratrol. However, an aqueous dispersion of the resveratrol-phospholipid complex is not stable because the resveratrol-phospholipid complex is poorly dispersed in water, crystallization of the resveratrol occurs and therefore the resveratrol is easily precipitated from the aqueous dispersion of the complex. These disadvantages limit the application of resveratrol-phospholipid complex in formulating, for example, a resveratrol injection solution, an oral liquid, or a spray formulation for skin care.

DISCLOSURE OF THE INVENTION

One object of the present invention is to provide a bioavailable nanoemulsion of resveratrol-phospholipid complex, which exhibits high stability and excellent water solubility.

Another object of the present invention is to provide a method for preparing the nanoemulsion of resveratrol-phospholipid complex.

A further object of the present invention is to provide the applications of the nanoemulsion of resveratrol-phospholipid complex in the field of cosmetics, pharmaceuticals and health products.

The technical solutions of the present invention are as follows:

A nanoemulsion of resveratrol-phospholipid complex, comprises: 1 part by weight of resveratrol, 2~30 parts by weight of phospholipids and 30~490 parts by weight of an aqueous solution of polyol, and the concentration of the polyol in the aqueous solution is 30~99 percent by weight; the nanoemulsion is miscible with water at any ratio, and the particle diameter of the resveratrol-phospholipid complex in the nanoemulsion is less than 200 nm. Preferably, the 1 part by weight of resveratrol and the 2~30 parts by weight of phospholipid firstly form a resveratrol-phospholipid complex; then the resveratrol-phospholipid complex is mixed with the 30~490 parts by weight of the aqueous solution of polyol to form the nanoemulsion of resveratrol-phospholipid complex. Preferably, the resveratrol is cis-resveratrol or trans-resveratrol; the phospholipid is at least one member selected from the group consisting of soybean lecithin, egg lecithin, cephalin, sphingomyelin, cardiolipin, lipositol; and the polyol is at least one member selected from the group consisting of glycerine, propylene glycol, 1,3-butanediol, oligosaccharide (n≦10), or polyethylene glycol 200~800. Examples of the oligosaccharide include: glucose oligosaccharides (n≦10), fructo-oligosaccharides (n≦10), or cyclic glucose oligosaccharides (n≦10) and the like.

Preferably, the particle diameter of the resveratrol-phospholipid complex in the nanoemulsion is less than 100 nm. More preferably, the particle diameter of the resveratrol-phospholipid complex in the nanoemulsion is less than 50 nm.

Relative to 1 part by weight of resveratrol, the amount of phospholipid is preferably 5~25 parts by weight, more preferably 10~20 parts by weight.

Relative to 1 part by weight of resveratrol, the amount of the aqueous solution of polyol is preferably 50~400 parts by weight; and the polyol concentration of the aqueous solution is 50~99 percent by weight.

A method for preparing the nanoemulsion of the invention, comprises the following steps:

(1) stirring a mixture of 1 part by weight of resveratrol, 2~30 parts by weight of phospholipids and 0.5~5 parts by weight of solvent at 20~60° C. temperature until a transparent oily homogeneous liquid is obtained, wherein the solvent is at least one member selected from a group consisting of ethanol, acetone, ethyl acetate, methanol and ethyl ether;

(2) removing the solvent from the homogeneous liquid obtained in step (1) by vacuum distillation at 20~50° C. temperature to form a resveratrol-phospholipid complex;

(3) adding the resveratrol-phospholipid complex obtained in step (2) into 30~490 parts by weight of an aqueous solution of polyol at 20~60° C. temperature, and mixing the resulting mixture by stirring in the meantime of addition of the complex into the aqueous solution of polyol, thereby forming a crude dispersion (sometimes also called "crude emulsion" hereinafter) of resveratrol-phospholipid complex;

(4) homogenizing the crude dispersion obtained in step (3) by a high-pressure homogenizer or a Microfluidizer homogenizer for 2~10 times under a pressure of 200 bar to 1500 bar, thereby making the particle diameter of the resveratrol-phospholipid complex be less than 200 nm.

Preferably, the crude dispersion obtained in step (3) is homogenized by a high-pressure homogenizer or a Microfluidizer homogenizer for 3~8 times, under a pressure of 500 bar to 1500 bar.

The nanoemulsion described above is very useful in the fields of cosmetics, pharmaceuticals, and healthcare products.

The nanoemulsion of the invention is a potential medicament useful for reducing blood viscosity, inhibiting platelet coagulation and improving vasodilation to maintain blood flow; and also it can be used in the prevention or treatment of atherosclerosis, coronary heart disease, ischemic heart disease, high blood cholesterol, and a cancer, such as breast cancer.

The present invention also provides a pharmaceutical composition or a healthcare composition comprising the nanoemulsion of the invention as an active ingredient. The composition may be in any form of dosage, such as oral solutions, injections, powders, tablets, or capsules. The composition may be administrated by oral administration or may be administered via subcutaneous injection, intravenous injection or intramuscular injection.

For example, the nanoemulsion of the present invention may be directly formulated into oral solutions, or injections. The oral solutions, or injections may be readily prepared by mixing the nanoemulsion with pharmaceutically acceptable liquid excipients, such as water, salines, phosphate buffers or albumin solutions.

The nanoemulsion of present invention may be readily prepared into various oral or injection solutions by applying any known methods in the field. The concentration of the solution may range from 1 to 5,000 µg nanoemulsion per milliliter of the solution.

The excipients may be a liquid such as water, salines, phosphate buffers or albumin solutions. The nanoemulsion can be dried into powders, for example, by means of freeze drying. The dried powders of the nanoemulsion of the present invention may also be formulated into tablets, or capsules with a suitable solid excipient, such as antioxidant agents, starches or dextrins.

The composition comprising the nanoemulsion of the present invention as an active ingredient may be administrated to patients in a dosage, e.g. in the range of 1 to 5,000 µg per kilogram of body weight per day. The dosage will be determined by a medically qualified physician, based on a variety of factors of the patients or the takers, including age, weight, severity of sickness, the cause and history of the disease, and other health conditions.

The nanoemulsion of the present invention can also be made into a cosmetic to be used in particular for slowing down the ageing and cell degeneration processes, the cosmetic composition according to the present invention is preferably in the form of a cream, gel, ointment and emulsion.

The present nanoemulsion of resveratrol-phospholipid complex possesses the following properties and advantages:
1. The nanoemulsion is a viscous transparent liquid product, and it is very stable under cold or hot storage conditions;
2. The nanoemulsion has excellent water-solubility, thus can be diluted with water at any ratio and there will be no precipitation of resveratrol due to crystallization;
3. The particle diameter of resveratrol-phospholipid complex in the nanoemulsion is less than 200 nm, preferably less than 100 nm, more preferably less than 50 nm, thereby the bioavailability of resveratrol can be significantly improved.

BEST MODE OF CARRYING OUT THE INVENTION

The present invention will be described in detail hereinafter referring to the examples. However, the examples are used to illustrate the invention and are not intend to limit the scope of the invention. Where the specific conditions are not provided, the examples are carried out following the conventional conditions in the art or conditions proposed by the manufacturers.

Example 1

1 g trans-resveratrol (manufactured by Nanjing TCM Institute of Chinese Materia Medica), 2 g soybean lecithin (manufactured by Cargill Texturizing Solutions Deutschland GmbH & Co. KG) and 0.5 g ethanol were added into a beaker and stirred at 60° C. for 2 hrs to form a solution; then the ethanol was removed from the resulting solution under vacuum distillation at 40° C. for 4 hr thereby forming a resveratrol-phospholipid complex. Next, a crude emulsion of resveratrol-phospholipid complex was formed by stirring the obtained resveratrol-phospholipid complex with 30 g aqueous solution of glycerol (60 percent by weight) at 20° C. Then, a nanoemulsion of resveratrol-phospholipid complex was formed by homogenizing the crude emulsion in a high pressure homogenizer (manufactured by Niro Soavi S.p.A.) at a pressure of 500 bar and this homogenization was repeated 4 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 2

1 g trans-resveratrol, 15 g soybean lecithin, 15 g egg lecithin and 5 g ethyl ether were added into a beaker and stirred at 30° C. for 2 hrs to form a solution; then the ethyl ether was removed from the resulting solution under vacuum distillation at 20° C. for 4 hrs thereby forming a resveratrol-phospholipid complex. Next, a crude emulsion of the resveratrol-phospholipid complex was formed by stirring the obtained resveratrol-phospholipid complex with 490 g aqueous solution of glycerol (99 percent by weight) at 35° C. Then, a nanoemulsion of the resveratrol-phospholipid complex was formed by homogenizing the crude emulsion in a high pressure homogenizer at a pressure of 1500 bar, and this homogenization was repeated 1 time. The particle diameter of resveratrol-phospholipid complex in the resulted nanoemulsion was evaluated by using a laser scattering particle analyzer (Zetasize 3000, Malvern Inc.). The result is shown in Table 1 below.

Example 3

1 g cis-resveratrol, 15 g egg lecithin (manufactured by Cargill Texturizing Solutions Deutschland GmbH & Co. KG) and 2.5 g ethyl acetate were added into a beaker and stirred at 25° C. for 2 hrs to form a solution; then the ethyl acetate was removed from the resulting solution under vacuum distillation at 45° C. for 5 hrs thereby forming a resveratrol-phospholipid complex. Next, a crude emulsion of resveratrol-phospholipid complex was formed by stirring the obtained resveratrol-phospholipid complex with 200 g aqueous solution of propylene glycol (30 percent by weight) at 60° C. Then, a nanoemulsion of the resveratrol-phospholipid complex was formed by homogenizing the crude emulsion in a high pressure homogenizer at a pressure of 1,000 bar, and this homogenization was repeated 4 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 4

1 g trans-resveratrol, 5 g cephalin and 0.5 g acetone were added into a beaker and stirred at 50° C. for 2 hrs to form a solution; then, the acetone was removed from the resulting solution under vacuum distillation at 40° C. for 5 hr, thereby forming a resveratrol-phospholipid complex. Next, a crude emulsion of the resveratrol-phospholipid complex was formed by stirring the obtained resveratrol-phospholipid complex with 50 g aqueous solution of propylene glycol (60 percent by weight) at 50° C. Then, a nanoemulsion of the resveratrol-phospholipid complex was formed by homogenizing the obtained crude emulsion in a high pressure homogenizer at a pressure of 500 bar, and this homogenization was repeated 4 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 5

1 g trans-resveratrol, 10 g sphingomyelin and 1 g methanol were added into a beaker and stirred at 35° C. for 2 hrs to form a solution; then the methanol was removed from the resulting solution under vacuum distillation at 40° C. for 4 hrs, thereby forming a resveratrol-phospholipid complex. Next, a crude emulsion of the resveratrol-phospholipid complex was formed by stirring the obtained resveratrol-phospholipid complex with 100 g aqueous solution of 1,3-butanediol (80 percent by weight) at 45° C. Then, a nanoemulsion of the resveratrol-phospholipid complex was formed by homogenizing the crude emulsion in a high pressure homogenizer at a pressure of 800 bar, and this homogenization was repeated 4 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 6

1 g trans-resveratrol, 25 g soybean lecithin and 1.5 g absolute ethanol were added into a beaker and stirred at 25° C. for 2 hrs; then the ethanol was removed from the resulting solution under vacuum distillation at 35° C. for 5 hrs, thereby forming a resveratrol-phospholipid complex. Next, a crude emulsion of the resveratrol-phospholipid complex was formed by stirring the obtained resveratrol-phospholipid complex with 400 g aqueous solution of polyethylene glycol 200 (40 percent by weight) at 40° C., Then, a nanoemulsion of the resveratrol-phospholipid complex was formed by homogenizing the crude emulsion in a high pressure homogenizer at a pressure of 800 bar, and this homogenization was repeated 3 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 7

1 g trans-resveratrol, 8 g cardiolipin and 2 g absolute ethanol were added into a beaker and stirred at 40° C. for 2 hrs to form a solution; then the ethanol was removed from the resulting solution under vacuum distillation at 40° C. for 4 hrs, thereby forming a resveratrol-phospholipid complex. Next, a crude emulsion of the resveratrol-phospholipid complex was formed by stirring the obtained resveratrol-phospholipid complex with 100 g aqueous solution of polyethylene glycol 400 (50 percent by weight) at 35° C. Then, a nanoemulsion of the resveratrol-phospholipid complex was formed by homogenizing the crude emulsion in a high pressure homogenizer at a pressure of 1,000 bar pressure, and this homogenization was repeated 2 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 8

1 g trans-resveratrol, 20 g lipositol and 1.5 g absolute ethanol were added into a beaker and stirred at 50° C. for 2 hrs to form a solution; then the ethanol was removed from the resulting solution under vacuum distillation at 40° C. for 4 hrs, thereby forming a resveratrol-phospholipid complex. Next, a crude emulsion of the resveratrol-phospholipid complex was formed by stirring the obtained resveratrol-phospholipid complex with 180 g aqueous solution of polyethylene glycol 800 (30 percent by weight) at 45° C. Then, a nanoemulsion of the resveratrol-phospholipid complex was formed by homogenizing the crude emulsion in a Microfluidizer homogenizer (USA, MFIC Co., Ltd) at a pressure of 1200 bar, and this homogenization was repeated 5 times. The particle diameter of resveratrol-phospholipid complex in the resulted nanoemulsion was evaluated by using a laser scattering particle analyzer (Zetasize 3000, Malvern Inc.). The result is shown in Table 1 below.

Example 9

1 g trans-resveratrol, 6 g soybean lecithin and 1 g ethanol were added into a beaker and stirred at 35° C. for 2 hrs to form a solution; then the ethanol was removed from the resulting solution under vacuum distillation at 35° C. for 4 hrs, thereby forming a resveratrol-phospholipid complex. Next, a crude emulsion of the resveratrol-phospholipid complex was formed by stirring the obtained resveratrol-phospholipid complex with 250 g aqueous solution of fructooligosaccharides (Shandong Baolingbao Biotechnology Co., Ltd.) (50 percent by weight) at 35° C. Then, a nanoemulsion of the resveratrol-phospholipid complex was formed by homogenizing the crude emulsion in a high pressure homogenizer at a pressure of 1,000 bar pressure, and this homogenization was repeated 1 time. The particle diameter of resveratrol-phospholipid complex in the resulted nanoemulsion was evaluated by using a laser scattering particle analyzer (Zetasize 3000, Malvern Inc.). The result is shown in Table 1 below.

Example 10

1 g trans-resveratrol, 6 g soybean lecithin and 1 g ethanol were added into a beaker and stirred at 35° C. for 2 hrs to form a solution; then the ethanol was removed from the resulting solution under vacuum distillation at 35° C. for 4 hr, thereby forming a resveratrol-phospholipid complex. Next, a crude emulsion of the resveratrol-phospholipid complex was formed by stirring the obtained resveratrol-phospholipid complex with 100 g aqueous solution of cyclic glucose oligosaccharides (Shandong Baolingbao Biotechnology Co., Ltd.) (60 percent by weight) at 35° C. Then, a nanoemulsion of the resveratrol-phospholipid complex was formed by homogenizing the crude emulsion in a high pressure homogenizer at a pressure of 1,000 bar, and this homogenization was repeated 1 time. The particle diameter of resveratrol-phospholipid complex in the resulted nanoemulsion was evaluated by using a laser scattering particle analyzer (Zetasize 3000, Malvern Inc.). The result is shown in Table 1 below.

TABLE 1

Particle Diameter of the Resveratrol-Phospholipid Complex

| Formulation | Particle diameter/nm |
| --- | --- |
| Example 1 | 157 |
| Example 2 | 189 |
| Example 3 | 48 |
| Example 4 | 79 |
| Example 5 | 39 |
| Example 6 | 73 |
| Example 7 | 41 |
| Example 8 | 63 |
| Example 9 | 71 |
| Example 10 | 22 |

Example 11

5 ml nanoemulsion of resveratrol-phospholipid complex obtained from each of Examples 1~10 was respectively diluted with deionized water to a dilution of 5 times, 10 times, 50 times, and 100 times. Then the diluted nanoemulsions of resveratrol-phospholipid complex were centrifuged at a speed of 4,000 rpm for 30 minutes at room temperature. Whether there is a precipitation in the water-diluted nanoemulsion was observed with naked eyes. The results are shown in table 2 below.

TABLE 2

Stability of the Nanoemulsions of Examples 1~10 upon Water Dilution

| Formulation | precipitation in the nanoemulsions upon water dilution | | | |
| --- | --- | --- | --- | --- |
| | 5 times | 10 times | 50 times | 100 times |
| Example 1 | No | No | No | No |
| Example 2 | No | No | No | No |
| Example 3 | No | No | No | No |
| Example 4 | No | No | No | No |
| Example 5 | No | No | No | No |
| Example 6 | No | No | No | No |
| Example 7 | No | No | No | No |
| Example 8 | No | No | No | No |
| Example 9 | No | No | No | No |
| Example 10 | No | No | No | No |

Example 12

A sample of 10 ml nanoemulsion obtained from Example 1 was added to a glass test tube and the tube was sealed. Then the nanoemulsion contained in the tube was frozen by placing the tube in a thermostatic bath at −20° C. for 24 hrs. Following up this freezing treatment, the frozen sample was thawed by placing the tube in a thermostatic bath at 40° C. for 24 hrs. Subsequently, the freezing and then thawing treatment steps were repeated 2 times. Finally, 0.5 ml of the nanoemulsion subjected to the above-described freezing and thawing treatments was diluted 50 times with water, and then the diluted nanoemulsion was scattered with a laser scattering particle analyzer (Zetasize 3000, Malvern Inc.) to evaluate the particle diameter of the resveratrol-phospholipid complex. In addition, 0.5 ml of the nanoemulsion of Example 1, without subjecting to the above-described freezing and thawing treatments, was directly diluted 50 times with water, and then the diluted nanoemulsion was also scattered with a laser scattering particle analyzer (Zetasize 3000, Malvern Inc.) to evaluate the particle diameter of the resveratrol-phospholipid complex.

Similarly, a sample of the nanoemulsions obtained from each of Examples 2-10 was treated and evaluated in the same way as described above with respect to the sample of Example 1.

The results are shown in table 3 below.

TABLE 3

Particle Diameter of the Resveratrol-Phospholipid Complex Nanoemulsion Without/With Freezing and Thawing Treatment

| Formulation | Particle diameter (nm) without freezing and thawing treatment | Particle diameter (nm) upon freezing and thawing treatment |
| --- | --- | --- |
| Example 1 | 157 | 164 |
| Example 2 | 189 | 178 |
| Example 3 | 48 | 51 |
| Example 4 | 79 | 73 |
| Example 5 | 39 | 44 |
| Example 6 | 73 | 79 |
| Example 7 | 41 | 47 |
| Example 8 | 63 | 61 |
| Example 9 | 71 | 79 |
| Example 10 | 22 | 25 |

The present invention is not limited by the specific Examples described above, and it can be appreciated by a person skilled in the field to which the present invention pertains that various modifications can be made to the invention without departing from the spirit thereof. And, these modifications fall into the scope of the present invention.

What is claimed is:

1. A nanoemulsion of resveratrol-phospholipid complex comprising: 1 part by weight of resveratrol, 10-20 parts by weight of phospholipids, and 30-490 parts by weight of an aqueous solution of a polyol, the concentration of the polyol in the aqueous solution being 30-99 percent by weight of the aqueous solution; wherein the nanoemulsion is miscible with water at any ratio, and the particle diameter of the resveratrol-phospholipid complex in the nanoemulsion is less than 200 nm.

2. The nanoemulsion according to claim 1, wherein the resveratrol is cis-resveratrol or trans-resveratrol; the phospholipid is at least one member selected from the group consisting of soybean lecithin, egg lecithin, cephalin, sphingomyelin, cardiolipin, lipositol; and the polyol is at least one member selected from the group consisting of glycerine, propylene glycol, 1,3-butanediol, oligosaccharides (n≦10), and polyethylene glycol 200-800.

3. The nanoemulsion according to claim 1, wherein the particle diameter of the resveratrol-phospholipid complex is less than 100 nm.

4. The nanoemulsion according to claim 1, wherein the particle diameter of the resveratrol-phospholipid complex is less than 50 nm.

5. The nanoemulsion according to claim 1, wherein the amount of the aqueous solution is 50-400 parts by weight; and the polyol concentration of the aqueous solution is 50-99 percent by weight of the aqueous solution.

6. The nanoemulsion according to claim 1, wherein the 1 part by weight of resveratrol and the 10-20 parts by weight of phospholipid firstly form a resveratrol-phospholipid complex; then the obtained resveratrol-phospholipid complex is mixed with the 30-490 parts by weight of the aqueous solution of polyol.

7. A method for preparing a nanoemulsion comprising the following steps:
  (1) stirring a mixture of 1 part by weight of resveratrol, 10-20 parts by weight of phospholipid and 0.5-5 parts by weight of a solvent at 20-60° C. until a transparent oily homogeneous liquid is obtained, wherein the solvent is at least one member selected from a group consisting of ethanol, acetone, ethyl acetate, methanol, and ethyl ether;
  (2) removing the solvent from the homogeneous liquid obtained in step (1) by vacuum distillation at 20-50° C. to form a resveratrol-phospholipid complex;
  (3) adding the resveratrol-phospholipid complex obtained in step (2) into 30-490 parts by weight of an aqueous solution of polyol at 20-60° C. temperature, and mixing by stirring in the meantime of the addition of the resveratrol-phospholipid complex into the aqueous solution, thereby forming a crude dispersion of resveratrol-phospholipid complex;
  (4) homogenizing the crude dispersion obtained in step (3) with a high-pressure homogenizer or a Microfluidizer homogenizer for 2-10 times under a pressure of 200 bar to 1500 bar, thereby making the particle diameter of the resveratrol-phospholipid complex less than 200 nm.

8. The method according to claim 7, wherein in step (4) the dispersion is homogenized for 3-8 times, under a pressure of 500 bar to 1500 bar.

* * * * *